(12) United States Patent
Lin

(10) Patent No.: US 6,722,879 B2
(45) Date of Patent: Apr. 20, 2004

(54) SCREW DEVICE FOR ORTHODONTIC TREATMENT

(76) Inventor: Cheng-Yi Lin, No. 190-1, WenHua Rd., PanChao, Taipei (TW)

( * ) Notice: Subject to any disclaimer, the term of this patent is extended or adjusted under 35 U.S.C. 154(b) by 0 days.

(21) Appl. No.: 10/359,577

(22) Filed: Feb. 7, 2003

(65) Prior Publication Data

US 2004/0023182 A1 Feb. 5, 2004

Related U.S. Application Data

(63) Continuation-in-part of application No. 10/211,037, filed on Aug. 5, 2002.
(51) Int. Cl.[7] ............................... A61C 3/00; A61C 8/00
(52) U.S. Cl. ........................................ 433/18; 433/173
(58) Field of Search ........................... 433/18, 173, 174

(56) References Cited

U.S. PATENT DOCUMENTS

| | | | | |
|---|---|---|---|---|
| 4,988,292 A | * | 1/1991 | Rosen | 433/17 |
| 5,071,345 A | * | 12/1991 | Rosen | 433/17 |
| 5,836,768 A | * | 11/1998 | Huskens et al. | 433/24 |
| 5,921,774 A | * | 7/1999 | Kanomi et al. | 433/18 |
| 6,241,516 B1 | * | 6/2001 | Orikasa et al. | 433/17 |
| 2002/0127510 A1 | * | 9/2002 | Kyung et al. | 433/18 |

* cited by examiner

Primary Examiner—Cary E. O'Connor
(74) Attorney, Agent, or Firm—Troxell Law Office PLLC

(57) ABSTRACT

A screw device for orthodontic treatment is formed with a platform part that has a relatively large radial width between a head part and a screw-body part of the screw device, and a neck part that has a radial width smaller than that of head part is also formed between the platform part and the head part. Therefore, a hook ring at the end of a spring (or rubber band) used for orthodontic treatment may be directly fitted from the head part and be positioned at the neck part without worrying about being dropped off The thickness of the platform part may prop the spring up the gingiva for keeping from friction. By screwing the screw-body part into the maxilla (or mandible) to make the platform part abutted against the maxilla (or mandible), not only may a stable screwing force be provided for securing the screw, but also does the side surface of the platform have a function of facilitating the gingiva tissue to grow, so the healed-over wound will be more even and good looking. The screw-head part of the invention may be arranged with slot for providing an accommodation for the orthodontic archwire. The screw of the invention not only may provide a hook-hanging mechanism for the spring, but also have a function for supporting the orthodontic archwire.

18 Claims, 10 Drawing Sheets

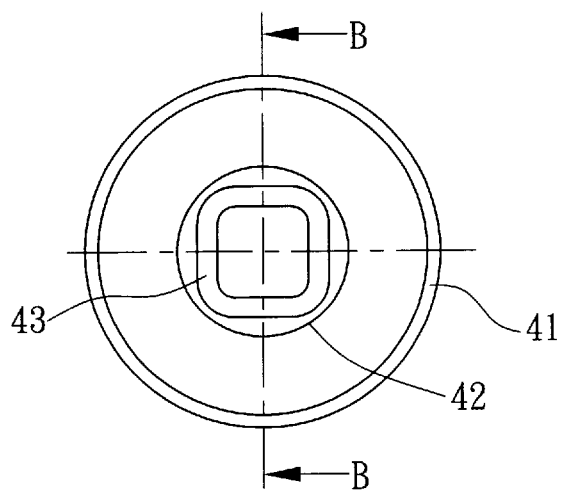
FIG. 6C
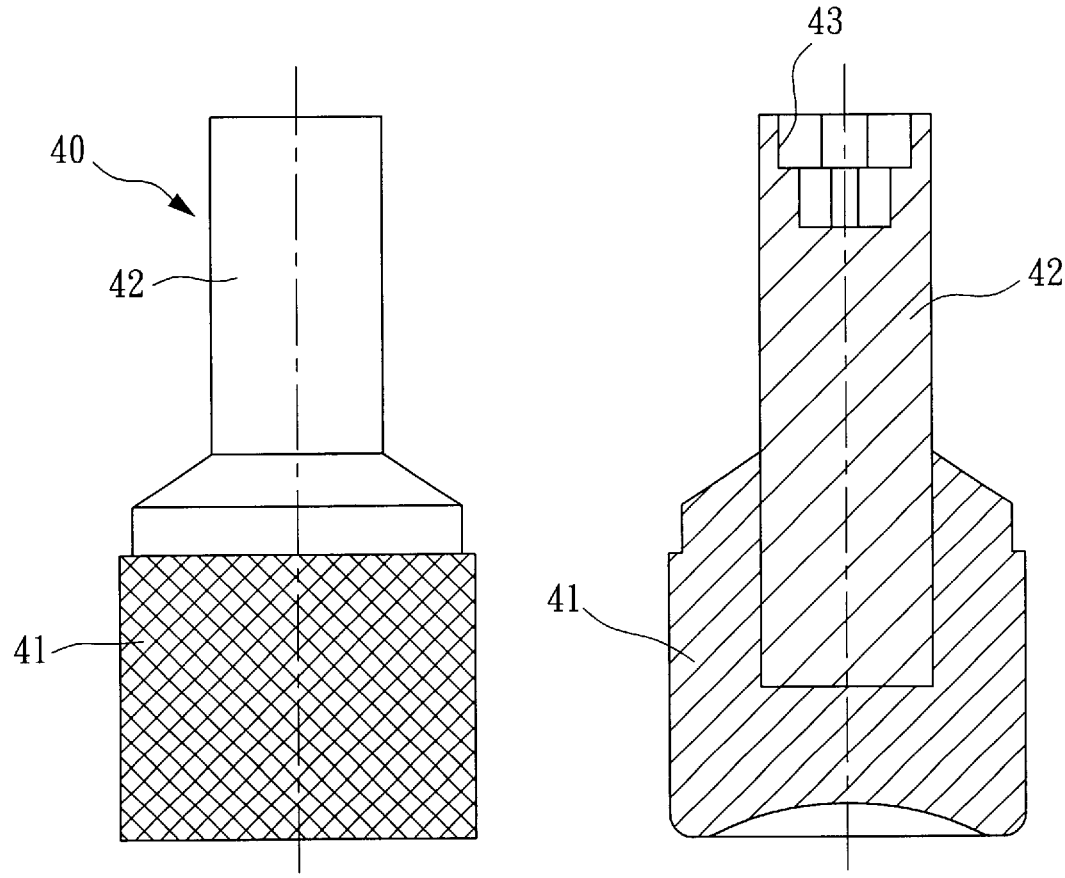
FIG. 6A
FIG. 6B

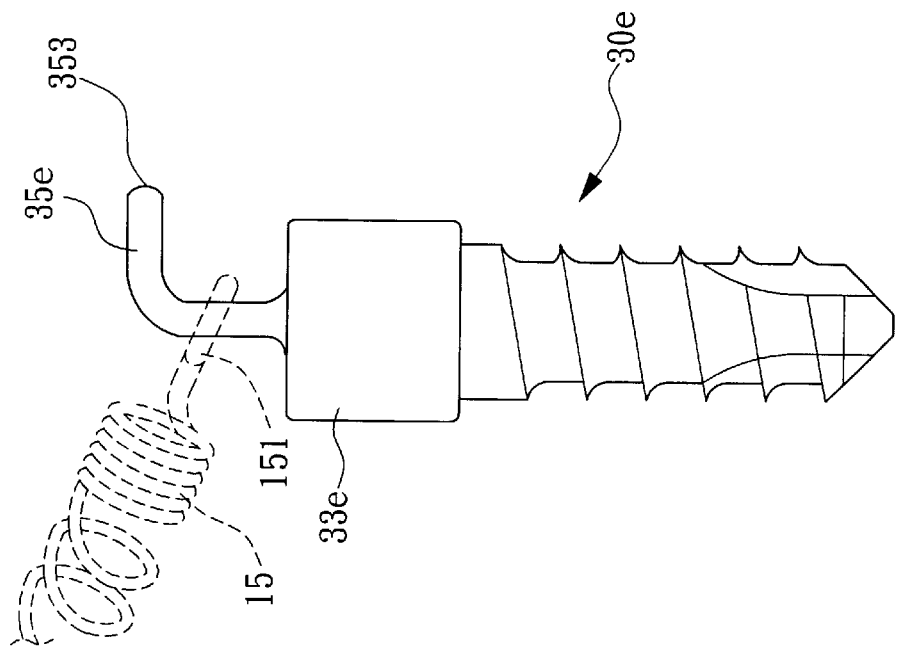
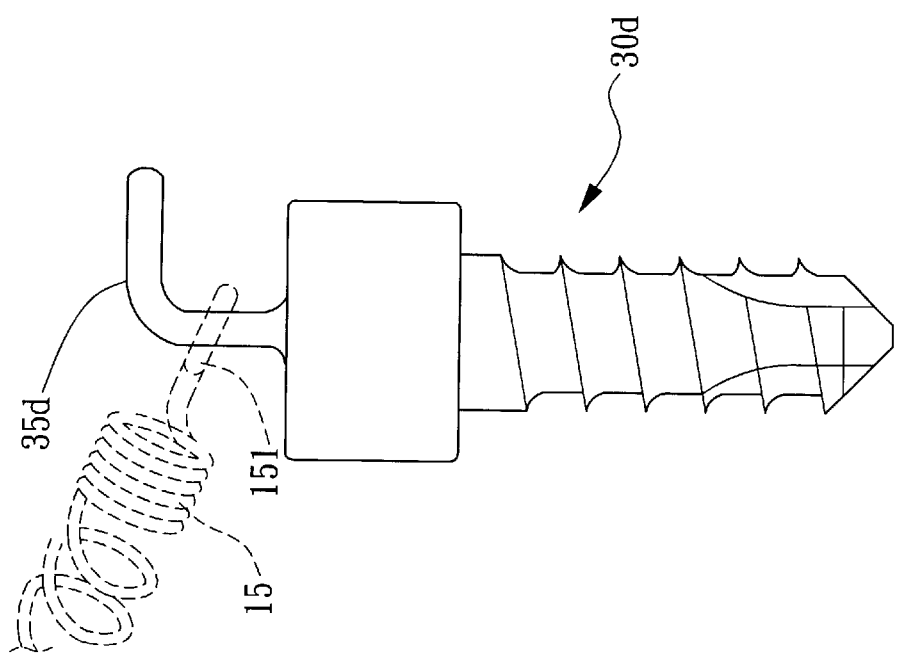

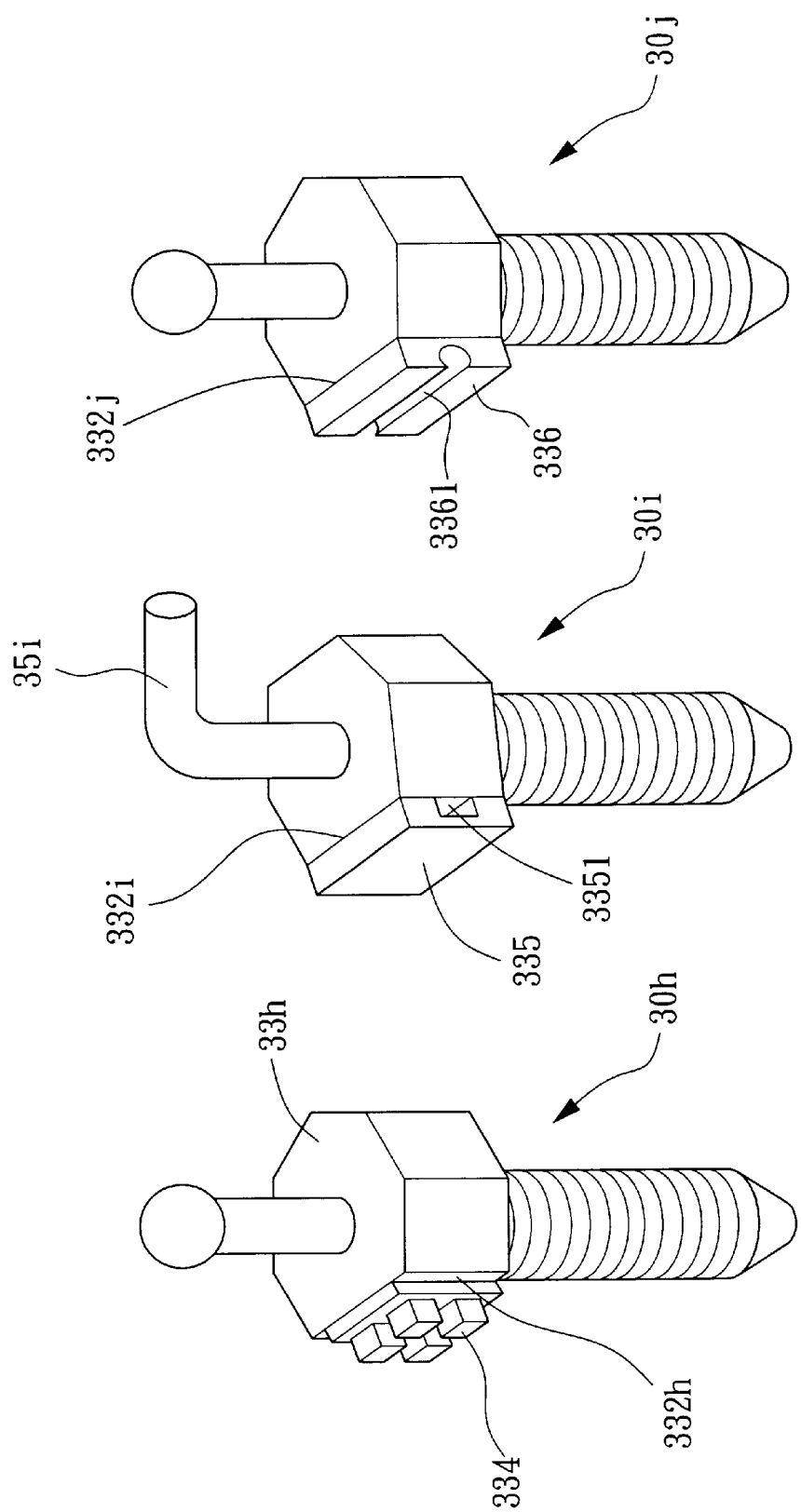

SCREW DEVICE FOR ORTHODONTIC TREATMENT

FIELD OF THE INVENTION

The invention relates to a screw device for orthodontic treatment, especially to a screw device that may be arranged in the maxilla (or mandible) and be capable of positioning the spring used for orthodontic treatment and accommodating the orthodontic archwire. This application is a continuation-in-part (CIP) application of U.S. patent application Ser. No. 10/211,037 filing date Aug. 5, 2002 which is now pending.

BACKGROUND OF THE INVENTION

As shown in FIG. 1, in a conventional orthodontic treatment process, after part of the maxilla (or mandible) 10 is cut off or a tooth 12 is pulled out (usually not the incisor), the tooth 12 or the maxilla. (or mandible) 10 is pulled and dragged by a orthodontic archwire 13 after the operation for helping the maxilla (or mandible) 10 to heal over or correcting the position of the tooth 12. In order to maintain the position of the orthodontic archwire 13 relative to the tooth 12, it is usually to apply several orthodontic brackets 14 adhered onto the tooth 12, and each orthodontic bracket 14 is arranged with slot 141 for providing an accommodation for the orthodontic archwire 13. The width and the depth of the slot 141 must be slightly larger than the diameter of the orthodontic archwire 13 such that, not only may the orthodontic archwire 13 be appropriately glided along the extensive direction of the slot 141, but also may the orthodontic archwire 13 be kept from being dropped out of the slot 141.

As known in the prior arts, in order to provide a pulling-and-dragging force to the orthodontic archwire 13, a screw 20 is screwed on a maxilla (or mandible) 10 at the adjacency of a molar 121, then a spring 15 or rubber band is further connected between the screw 20 and the end of the orthodontic archwire 13 for providing an appropriate pulling-and-dragging force. Since the end of this kind of spring 15 used specially for orthodontic treatment in current market is all arranged with a hook ring 151 so, for the connection between the spring 15 and the end of the orthodontic archwire 13, the end of the orthodontic archwire 13 just may be bent into a hook structure 131, then it can be easy to fit the hook ring 151 of the spring 15 into the hook structure 131 of the end of the orthodontic archwire 13, such that both connection is completed. Relatively, the connection between the spring 15 and the screw 20 is more difficult relatively.

As shown in FIG. 2 and FIG. 3, since the screw 20 currently applied for orthodontic treatment is all belonged to the common screw 20 as shown in FIG. 2 and FIG. 3, so the materials used for the screw 20, orthodontic bracket 14, and orthodontic archwire 13 are usually pure titanium alloy or stainless steel, those which are harmless to the human body. The screw 20 is commonly comprised of two parts: the head part 21 and the screw-body part 22. A general screw head groove 211 is then arranged on the head part 21 for providing a securing operation for a screwdriver (not shown in the figure). Usually, the dimension of the head part 21 is the widest part along the entire screw 20. Further, the diameter of the head part 21 is usually larger than the inner diameter of the hook ring 151 of the end of the spring 15, such that it is impossible for the spring to be hooked and hanged on the screw 20 directly. Therefore, for the current prior arts, an additional ligature wire 16 is used for tying the end of the spring 15 onto the screw-body part of the screw 20. However, such kind of method has caused several shortcomings as follows:

(1) It is difficult to operate. Since the head part 21 of the screw 20 is larger than the hook ring 151 of the spring 15, so it is impossible for the spring to be hooked and hanged on the screw 20 but, if the diameter of the head part 21 of this prior screw 20 is designed to be smaller than the hook ring 151 of the spring 15, then it will be much more easier for the spring 15 to be dropped off from the screw 20 to cause further inconvenience. Therefore, the prior arts that still use additional ligature wire 16 for tying the spring 15 and the screw 20 not only cause inconvenient in operation, but also cause difficulties for a less-experienced doctor to approach such kind of operation.

(2) It is easy for the spring 15 and the ligature wire 16 to impinge the gingiva 11. Since the ligature wire 16 is tied on the screw-body part 22 of the screw 20, so the ligature wire 16 and the spring 15 will be sometimes abutted against the gingiva 11 and irritate it. Not only will the user feel uncomfortable, but also may it sometimes hurt the gingiva 11 or reduce the healing-over speed of the wounds after operation.

(3) It is easy loosening for the screw 20. Since the screw-body part 22 of the screw 20 has a partial length that must be left in advance for tying the ligature wire 16 so, when the screw 20 is being driven tightly, it is impossible to screw the screw-body part 22 of the screw 20 completely into the maxilla (or mandible) 10 to make its head part 21 abutted smoothly against the maxilla (or mandible) 10. Contrarily, the head part 21 of the screw 20 must be kept an appropriate distance with the maxilla (or mandible) 10 for proceeding the operation of tying the ligature wire 16. In such way, the pulling-and-dragging force between the spring 15 and the ligature wire 16 will create a torque to the head part 21 of the screw 20, so it is easy to cause the screw 20 to loosen or even to drop off and break off.

(4) The gingiva 11 will be ugly after being healed over. Since the tissue of the gingiva 11 will be sometimes abutted against the screw 20 to grow during the healing procedure and there is a lack of appropriate guidance and restriction, so the surface of the gingiva 11 is uneven and ugly after being healing over.

(5) It only has a single function. This kind of prior screw 20 only can be applied in tying the ligature wire 16 for connecting the spring 15, neither does it have any other function, nor is it possible for providing an accommodation for the orthodontic archwire 13.

As known from above description, the prior arts that are used for orthodontic treatment currently still has many shortcomings to be further improved urgently.

SUMMARY OF THE INVENTION

The main objective of the invention is to provide an improvement for a screw device for orthodontic treatment. The invention has an easy operation for providing the spring to be hooked and hanged directly without worrying about being dropped off. It is also unnecessary to use additional ligature wire for tying the spring, so the spring may be propped up an appropriate height to have the advantage for avoiding any gingival irritation.

Another objective of the invention is to provide a screw device for orthodontic treatment to be able to screw the screw-body part of the screw completely into the maxilla (or mandible) for avoiding any looseness and the invention may further provide a side plane for guiding the gingiva's tissue to grow smoothly, such that the surface of the gingiva will be more beautiful after being healed over.

The further objective of the invention is to provide a screw device for orthodontic treatment to be able to further form a slot on the head part of the screw for providing an accommodation for the orthodontic archwire, such that the screw of the invention not only may provide the spring to be hooked and hanged, but also may have the function for supporting the orthodontic archwire in similarity to the orthodontic bracket.

In order to achieve above-mentioned objectives, in a preferred embodiment for the screw device for orthodontic treatment according to the invention, it is mainly to additionally arrange a platform part that has a relatively large dimension in radial width between the screw-body part and the head part of the screw and a neck part is also formed between the platform part and the head part. The radial width of the neck part is smaller than the head part, which is further smaller than the inner diameter of the hook ring of the spring. Therefore, the hook ring of the spring may be fitted directly into the head part and be positioned at the neck part without worrying about being loosened off. The thickness of the platform part may prop the spring up the gingiva for avoiding any irritation. By screwing the screw-body part into the maxilla (or mandible) to make the platform part be abutted against the maxilla (or mandible), not only may it provide a stable screwing force to make the screw uneasy to loosen, but also may the side surface of the platform have a function for guiding the gingiva's tissue to grow, so the wound will be more beautiful after being healed over. Preferably, the head part of the screw according to the invention is further arranged with slot for accommodating the orthodontic archwire, so the screw device according to the invention also has the function for supporting the orthodontic archwire in similarity to the orthodontic bracket in addition to provide the hooking and hanging function for the spring.

For further understanding the objects, the characteristics, and the functions of the structures of the present invention, a detailed description matched with corresponding drawings are presented as follows.

BRIEF DESCRIPTION OF THE DRAWINGS

FIGS. 6A, 6B, and 6C are respectively a front view, B—B sectional view and top view for a preferred embodiment for the screw device according to the invention for orthodontic treatment in matching with a screwdriver.

FIG. 9A is the fifth preferred embodiment for the screw device according to the invention for orthodontic treatment.

FIG. 9B is the sixth preferred embodiment for the screw device according to the invention for orthodontic treatment.

FIG. 11 is the eleventh preferred embodiment for the screw device according to the invention for orthodontic treatment.

FIG. 12 is the twelfth preferred embodiment for the screw device according to the invention for orthodontic treatment.

FIG. 13 is the thirteenth preferred embodiment for the screw device according to the invention for orthodontic treatment.

DETAILED DESCRIPTION OF THE INVENTION

One characteristic of the screw device for orthodontic treatment according to the invention is to additionally arrange a platform part that has a relatively large dimension in radial width between the screw-body part and the head part of the screw and a neck part is also formed between the platform part and the head part. The radial width of the neck part is smaller than the head part, which is further smaller than the inner diameter of the hook ring of the spring. Therefore, the hook ring of the spring may be fitted directly into the head part and be positioned at the neck part without worrying about being loosened off. The thickness of the platform part may prop the spring up the gingiva for avoiding any gingival irritation. By screwing the screw-body part into the maxilla (or mandible) to make the platform part be abutted against the maxilla (or mandible), not only may it provide a stable screwing force to make the screw uneasy to loosen, but also may the side surface of the platform have a function for guiding the gingiva tissue to grow, so the wound will be more beautiful after being healed over. Preferably, the head part of the screw according to the invention is further arranged with slot for accommodating the orthodontic archwire, so the screw device according to the invention also has the function for supporting the orthodontic archwire in similarity to the orthodontic bracket in addition to provide the hooking and hanging function for the spring.

Figure 1:
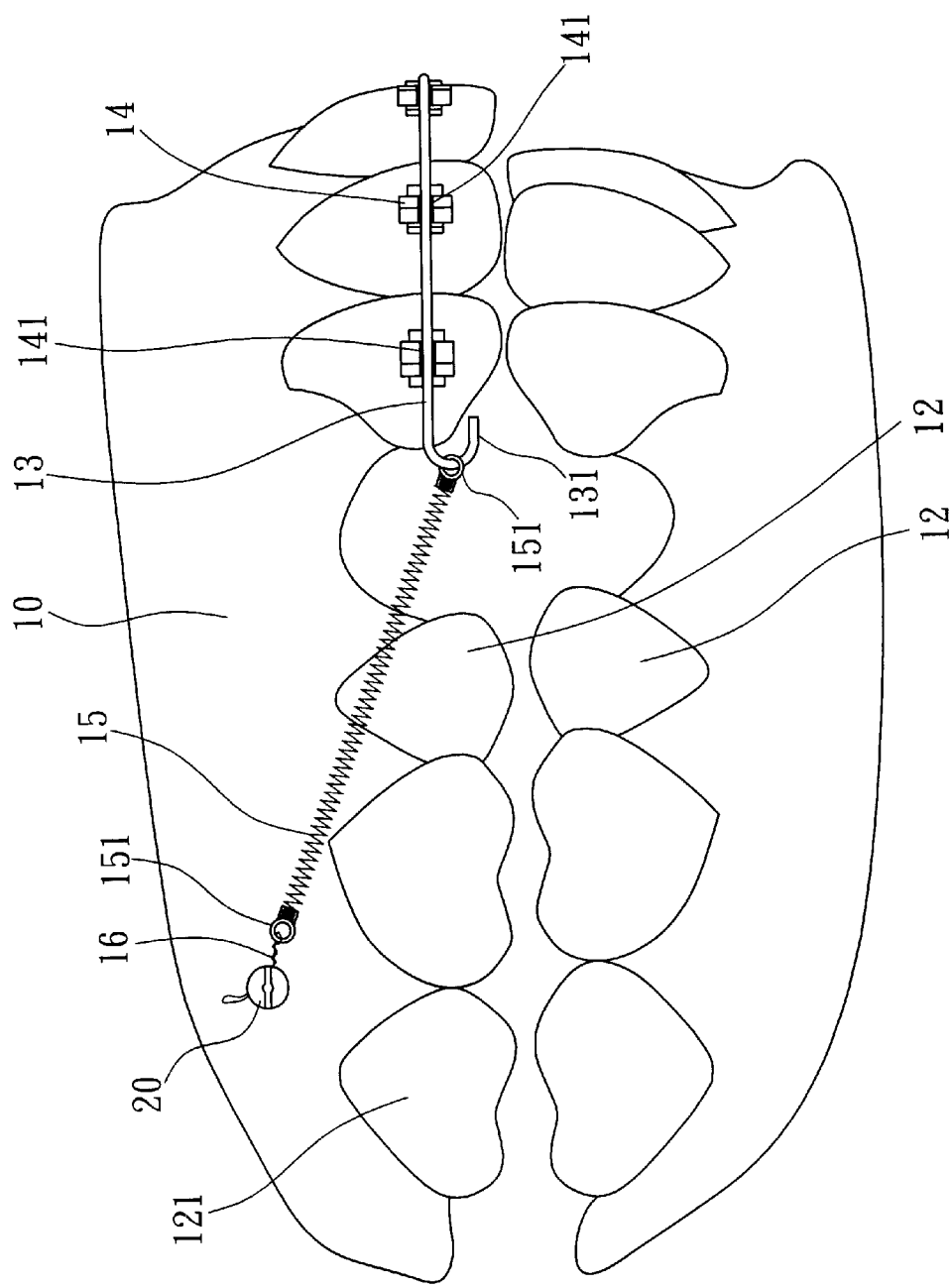
FIG. 1 is an embodiment illustration for a screw device, according to the prior arts, arranged in the mouth for orthodontic treatment.
Figure 2:
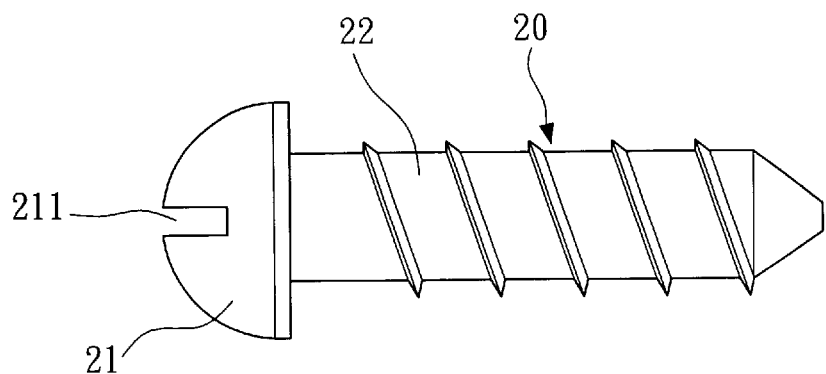
FIG. 2 is a front view for a screw according to the prior arts for orthodontic treatment.
Figure 3:
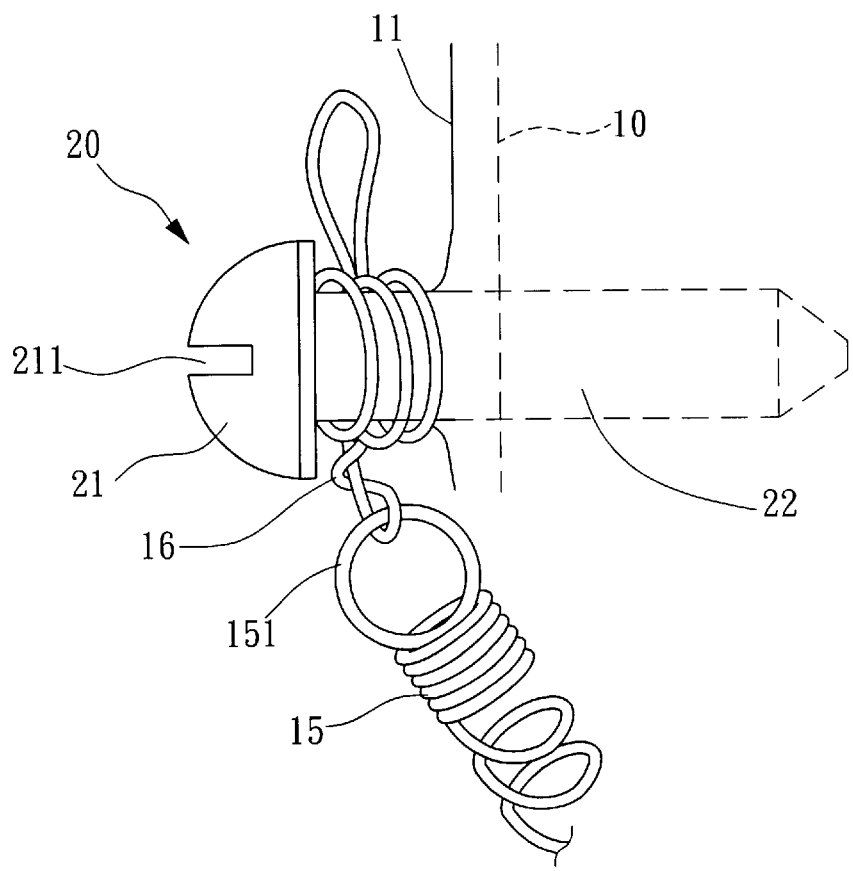
FIG. 3 is an illustration for tying and connecting an additional ligature wire with the spring and the screw according to the prior arts for orthodontic treatment.

The elements described thereinafter, such as: maxilla (or mandible) 10, gingiva 11, tooth 12, orthodontic archwire 13, orthodontic bracket 14, and spring 15 (or rubber band) for orthodontic treatment etc., and their relative position arranged in the mouth are all similar to the prior arts shown in FIG. 1 and they are not the technical characteristic of the invention, so they will be given same element names and referential numbers and their detailed composition, arrangement position, and function are not described herein repetitiously. One thing is worth mentioning: although the embodiment of the prior arts shown in FIG. 1 only depicts an embodiment that a correction device is arranged on the outside of the upper jaw, however, it may also be arranged on the outside or inside surface of maxilla (or mandible).

Figure 4A:
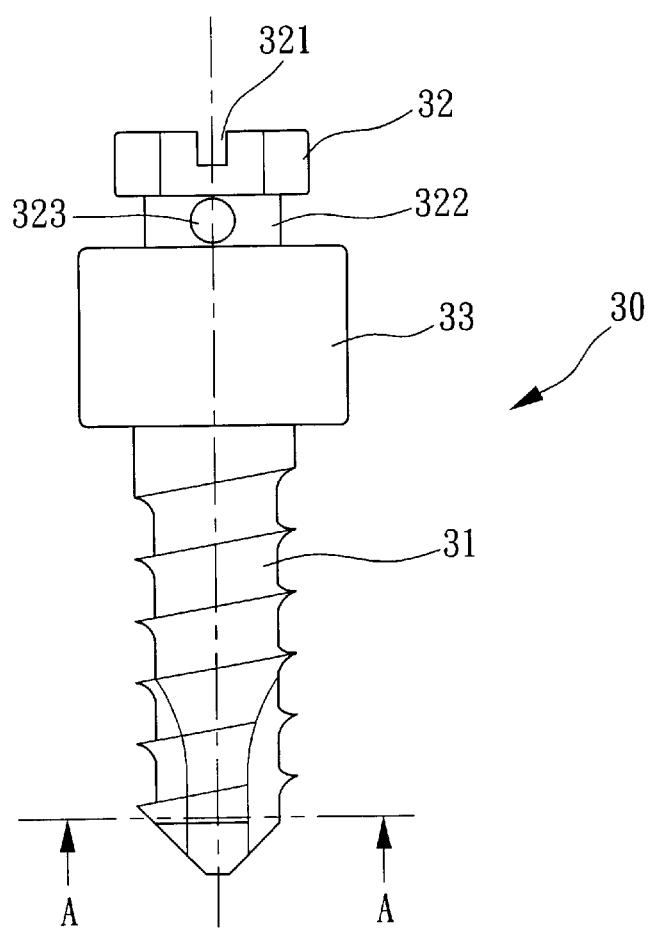
FIGS. 4A, 4B, and 4C are respectively a front view, top view, and A—A sectional view for the first preferred embodiment for the screw device according to the invention for orthodontic treatment.
Figures 4B, 4C:
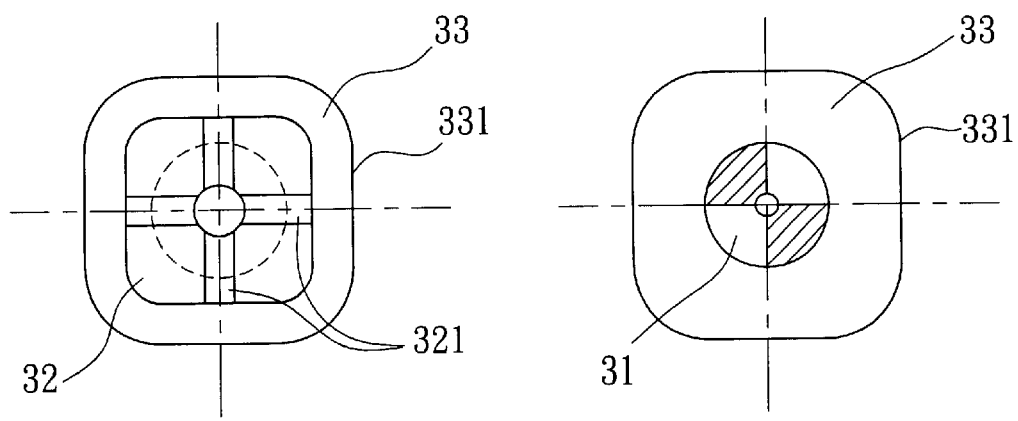
Figure 5:
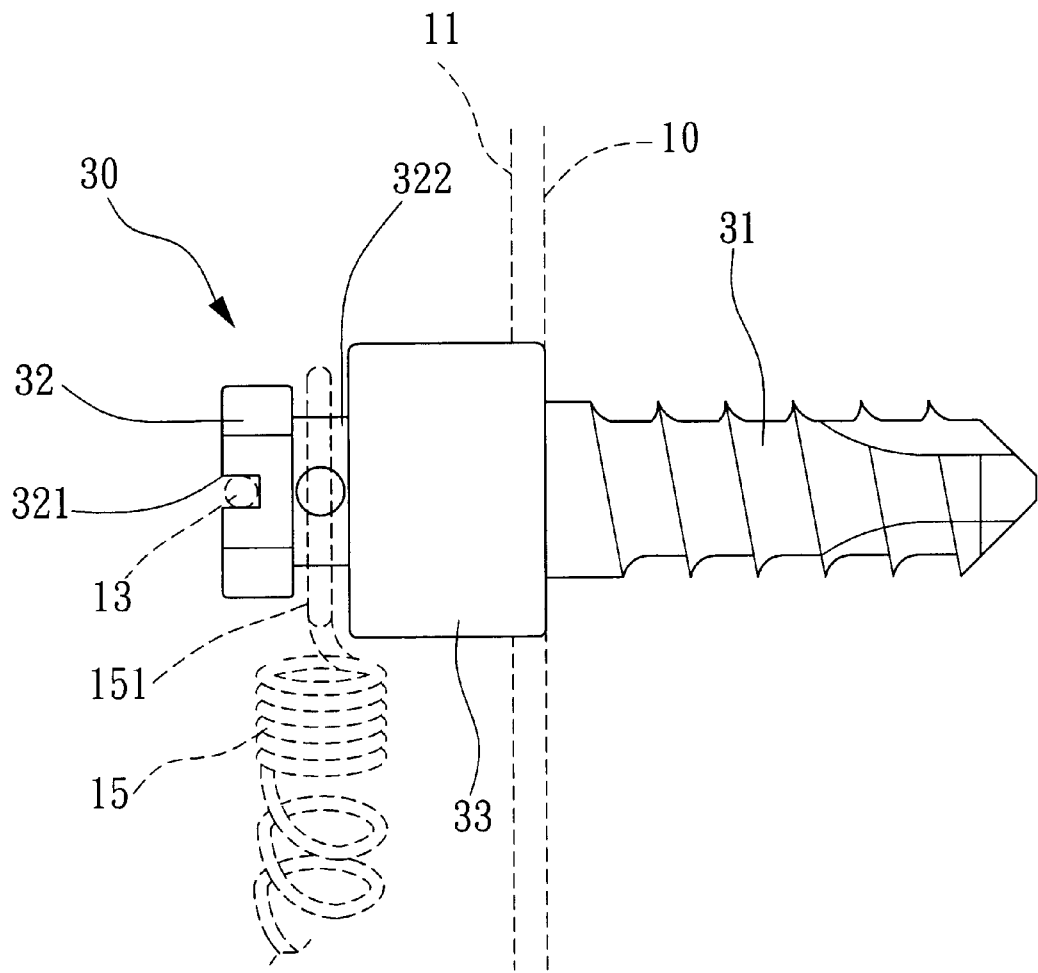
FIG. 5 is an illustration for a preferred embodiment for the screw device according to the invention for orthodontic treatment in matching with the spring and the orthodontic archwire, both which are arranged on the maxilla (or mandible) for orthodontic treatment.

Please refer to FIG. 4A to FIG. 4C, which are respectively a front view, top view, and A—A sectional view for a preferred embodiment for the screw device for orthodontic treatment according to the invention. FIG. 5 is an illustration for a preferred embodiment for the screw device 30 for orthodontic treatment according to the invention in matching with the spring 15 and the orthodontic archwire 13, both which are arranged on the maxilla (or mandible) 10 for orthodontic treatment.

As shown in FIG. 4A, FIG. 4B, FIG. 4C, and FIG. 5, in the preferred embodiment of the invention, the screw 30 for orthodontic treatment is integrally comprised of a screw-body part 31 of pillar shape, a head part 32, and a platform part 33. The materials of the screw 30 according to the invention may be titanium alloy or stainless steel or other rigid materials that are harmless to human body. The screw may be manufactured by a method of integral formation, or only the screw-body part 31 and the platform part 33 are manufactured integrally first, then the head part 32 is manufactured separately, and the head part 32 is then welded or glued onto the platform The screw-body part 31 is located at one side of the screw 31. The screw-body part 31 of pillar shape is extended an appropriate length along an axis and has a first diameter in the radial direction. On the screw-body part 31, there is screw tooth arranged for being screwed into the maxilla (or mandible) 10. The head part 32 is located at another side of the screw 30 corresponding to the screw-body part 31. The head part 32 has a first width in the said radial direction. The first width is usually smaller than the inner diameter of the hook ring 151 of the spring 15 for providing the hook ring 151 to be fitted directly into the head part 32 of the screw 30. In a preferred embodiment, the head part 32 may be designed in similarity to the prior orthodontic bracket 14 to have a structure of slot 321 extending in radial direction. The width and the depth included in the dimension of the slot 321 are preferably slightly larger than the diameter of the orthodontic archwire 13. General speaking, there are two kinds of dimension for the slot 141 of the prior current orthodontic bracket 14 and the slot 321 of the screw 30 of the invention: one is that the width and the depth are 0.022 inch and 0.028 inch respectively, and the other combination is 0.018 inch and 0.025 inch. Accommodating the orthodontic archwire 13 into the slot 321 of the head part 32 of the screw 30 will make the screw 30 of the invention provide a function similar to that of the prior orthodontic bracket 14 (as shown in FIG. 5).

The platform part 33 is connected between the screw-body part 31 and the head part 32, and the platform part 33 has an appropriate thickness in the axial direction and has a second width in the radial direction. Preferably, the second width is larger relatively. That is, the second width of the platform 33 is larger than the first width of the head part 32, the first diameter of the screw-body part 31, and the inner diameter of the hook ring of the spring 15. A neck part 322 is also formed at the connection place of the head part 32 and the platform part 33. At least one radial width of the neck part 322 is smaller than the first width of the head part 32 to make the neck part 322 become a part with narrowest width at a location relatively between the head part 32 and the platform part 33. The hook ring 151 of the spring 15 may be directly fitted into the head part 32, and be hooked and secured at the position of the neck part 322. One end of the spring 15 is connected to and secured on the screw 30 device. The thickness of the platform part 33 may keep the spring 15 from being abutted against the screw-body part 31.

Two side planes, of the platform part 33, adjacent to the screw-body part 31 and the head part 32 in the axial direction, are the planes that each has relatively larger area. Thereby, since the side plane, adjacent to the neck part 322, is wider than the diameter of the hook ring 151 of the spring 15, so it will become a working platform for facilitating a doctor in the operation of hooking and hanging the spring 15. Not only is the operation very easy, but also may the spring 15 be directly fitted, hooked, and hanged at the neck part 322 of the screw 30 completely without any worry of being dropped off, so it is absolutely unnecessary to apply additional ligature wire for tying the spring 15. Relatively, the side plane, at the outer contour of the platform part 33, having relatively larger area and smooth surface, will be beneficial in guiding the tissue of the gingiva 11 to grow during the healing over procedure of the wounds after operation, such that the surface of the gingiva 11 after being healing over is more even and beautiful. Furthermore, when the screw-body part 31 of the screw 31 of the invention is almost completely screwed into the maxilla (or mandible) 10, the lower side surface, of the platform part 33, at the adjacency of the screw-body part 31, will be approximately abutted against the surface of the maxilla (or mandible) 10. At this time, the platform part 33, of relatively larger area, will be able to keep the screw 30 from incurring loose phenomenon because of being forced. Of course, we may also choose that the screw-body part 31 is not completely screwed into the maxilla (or mandible) 10 and a gap is still left.

In this preferred embodiment, at least one penetration hole 323 of axial direction may further be arranged in the neck part 322 at the jointed place of the head part 32 and the platform part 33. The inner diameter of the penetration hole 323 may be larger than the diameter of the wire loop of the spring 15 or larger than the diameter of the orthodontic archwire 13. In another embodiment not shown in the figure, the wire of the end of the spring 15 (or the end of the orthodontic archwire 13)): may be directly fitted into the penetration hole 323 of the neck part 322 and wound around the outer contour of the neck part 322, such that an objective for securing and positioning the end of the spring 15 (or the end of the orthodontic archwire 13) to the screw 30 is achieved.

In this preferred embodiment, since the head part 32 of the screw 30 is designed as a slot 321 structure similar to the orthodontic bracket 14 capable of accommodating the orthodontic archwire 13, so a common screwdriver is inappropriate for screwing the screw 30 of the invention into the maxilla (or mandible) 10. If a common traditional screwdriver is used directly for screwing the screw 30 of the invention, then it is easy to deform or wear out the slot 321 on the head part 32, such that the slot 321 is no more appropriate for accommodating the orthodontic archwire 13. Therefore, the invention designs the outer contour in the radial direction of the platform 33 as a polygon contour 331 of a noncircular shape, such as the contour structure similar to a square and shown in FIG. 4B and FIG. 4C. This structure may be matched with an external screwdriver 40 specially designed for the screw 30 of the invention.

Please refer to FIG. 6A, 6B, and 6C, which are respectively a front view, B—B sectional view, and top view for a preferred embodiment for the screw 30 device for orthodontic treatment according to the invention in matching, with a screwdriver 40. The screwdriver 40 has a handle part 41 available for the user to grip, a rotation rod 42 extended out an appropriate distance from one side of the handle part 41, and a polygon recession seat 43 indented inwardly and arranged to the end of the rotation rod 42. The shape and the contour of the polygon recession seat 43 is just corresponded to and matched with the outer contour of the polygon contour 331 of the platform part 33. The recession depth and the shape of the polygon recession seat 43 may at least accommodate the head part 32 to make the polygon recession seat 43 inset onto the platform part 33. Gripping and rotating the handle part 41 may screw the screw 30 into or off the maxilla (or mandible) 10.

Figure 7:
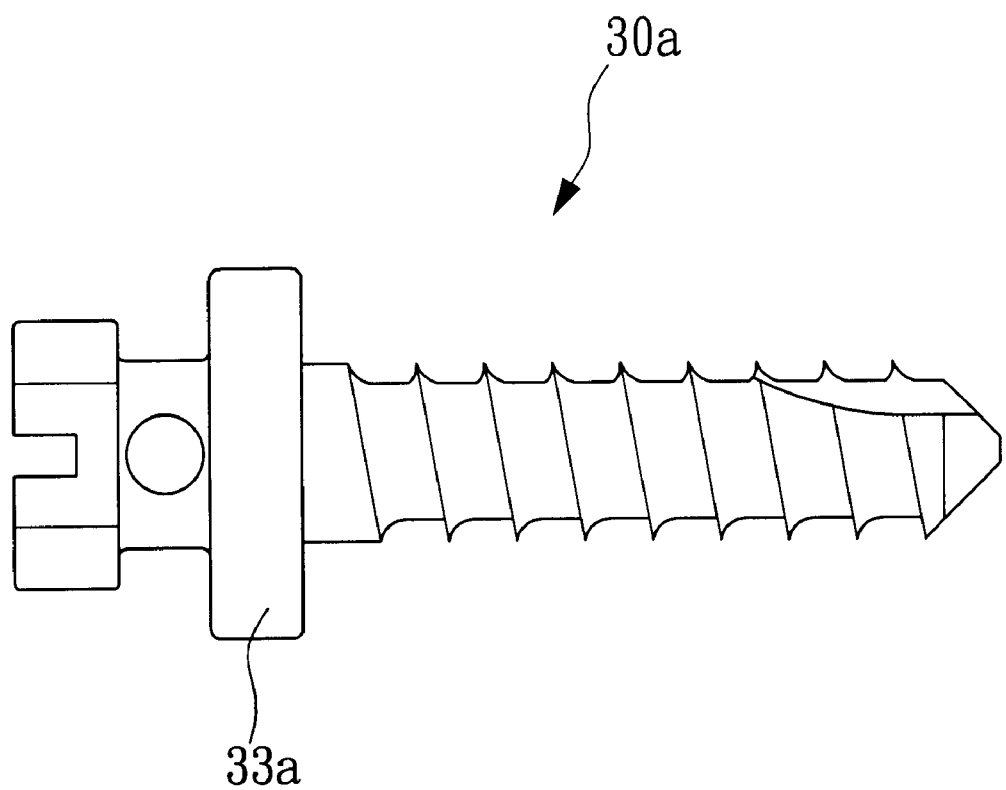
FIG. 7 is the second preferred embodiment for the screw device according to the invention for orthodontic treatment.
Figure 8A:
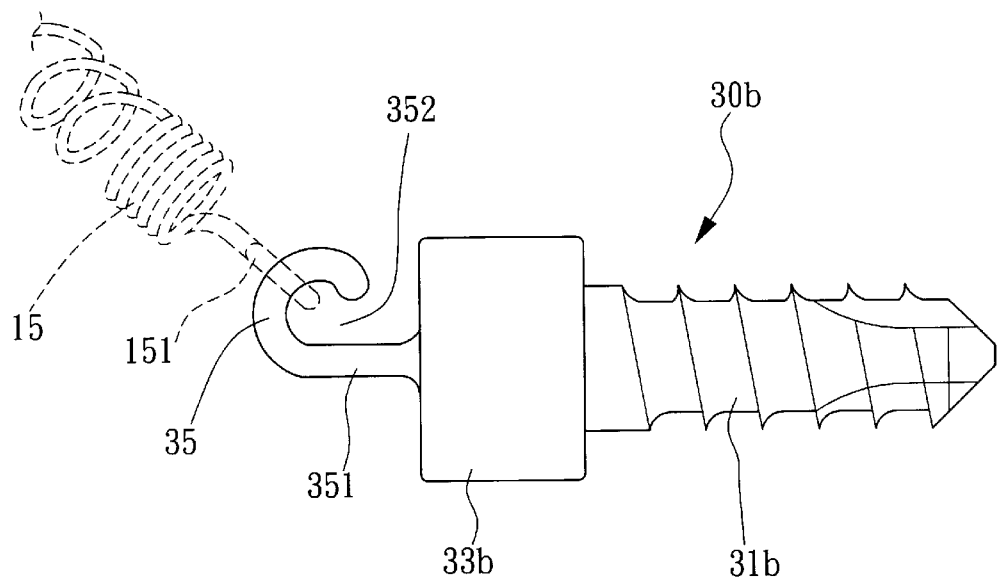
FIG. 8A is the third preferred embodiment for the screw device according to the invention for orthodontic treatment.

Please refer to FIG. 7, which is another preferred embodiment for the screw 30a device according to the invention for orthodontic treatment. In this preferred embodiment, most elements of the screw 30a are same as those shown in FIG. 4A, so a repetitious description is not presented herein any more. The only different point is that the platform part 33a of the screw embodiment shown in FIG. 7 has a relatively thinner thickness for being adapted to different requirement, for example, when the mouth's mucous membrane of the patient to be corrected is thinner. Please refer to FIG. 8A, which is a further preferred embodiment for the screw 30b device according to the invention for orthodontic treatment. In this preferred embodiment, most elements of the screw 30b are same as those of the embodiment shown in FIG. 4A. The screw 30b also has a screw-body part 31b, a platform part 33b, a head part 35, and a neck part 351. The different point of the screw 30b shown in FIG. 8A is that, in this embodiment, instead of showing a slot as a orthodontic bracket structure, the head part 35 of the screw 30b is designed extensively as a hook-shaped structure. In this embodiment, the head part 35 is wound by a wire to be shown as an arc shape for constituting the hook-shaped structure, and the arc-shaped wire is wound approximately to 180 degree to 300 degree for leaving a gap 352 for providing the hook ring 151 of the spring 15 to be fitted in. When the hook ring 151 of the spring 15 is hooked directly with the head part 35, the hook-shaped structure may keep the spring 15 from being dropped off.

Figure 8B:
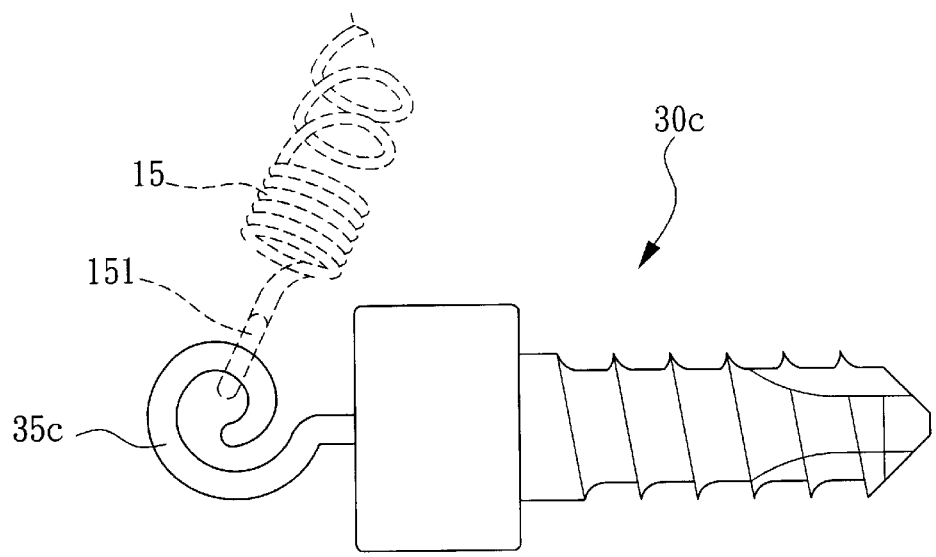
FIG. 8B is the forth preferred embodiment for the screw device according to the invention for orthodontic treatment.

Please refer to FIG. 8B, which is a further preferred embodiment for the screw 30c device according to the invention for orthodontic treatment. In this preferred embodiment, most elements of the screw 30c are same as those of the embodiment shown in FIG. 8A, so a repetitious description is skipped herein. The only one different point is that the head part 35c of the screw 30c shown in FIG. 8B is formed as a swirl-shaped structure by an arc-shaped wire wound at least 360 degrees, so it has better functions for the hook ring 151 of the spring 15 to be positioned and secured, no matter with which angle the spring is connected to the head part 35c of this screw 30c, it still can be kept from loosening off.

Please refer to FIG. 9A, which illustrates the fifth preferred embodiment for the screw device according to the invention for orthodontic treatment. In this preferred embodiment, most elements of the screw 30d are same as those of the embodiment shown in FIG. 8A, so a repetitious description is skipped herein. The only one different point is that the head part 35d of the screw 30d shown in FIG. 9A is formed as a reversed L-shaped structure by a wire bent at 90 degrees, so it has the benefit of being simple structure and easy to be manufactured.

FIG. 9B is the sixth preferred embodiment for the screw device according to the invention for orthodontic treatment. In this preferred embodiment, most elements of the screw 30e are same as those of the embodiment shown in FIG. 9A, so a repetitious description is skipped herein. The only one different point is that the platform part 33e of the screw 30e is narrower than which of the screw 30d shown in FIG. 9A. Moreover, the leading end 353 of the head part 35 is extending out of the outer contour of the narrowed platform part 33e.

Figure 9C:
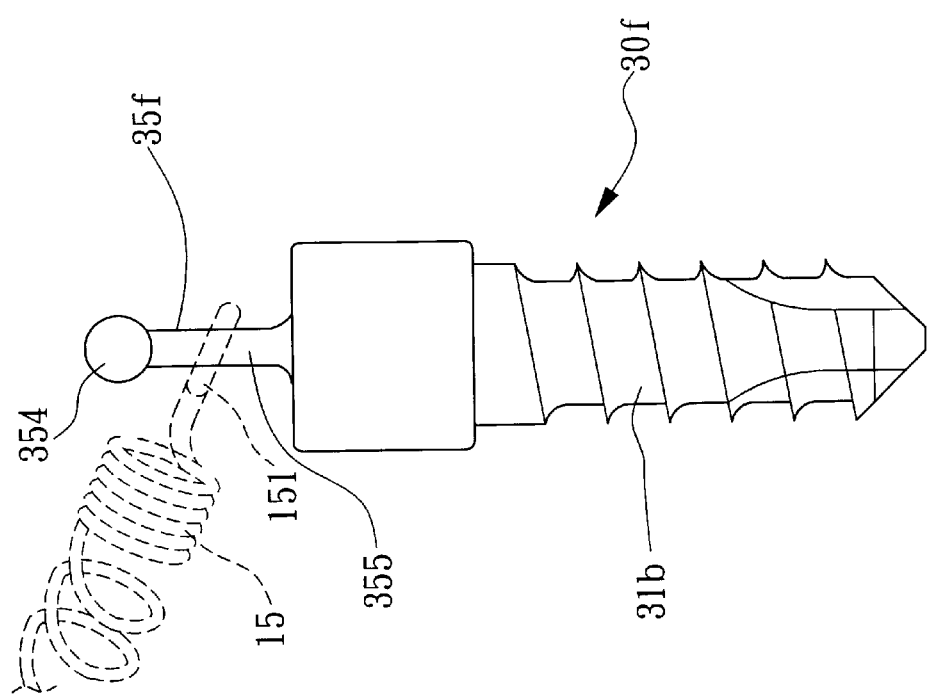
FIG. 9C is the seventh preferred embodiment for the screw device according to the invention for orthodontic treatment.

FIG. 9C is the seventh preferred embodiment for the screw device according to the invention for orthodontic treatment. In this preferred embodiment, most elements of the screw 30f are same as those of the embodiment shown in FIG. 9B, so a repetitious description is skipped herein. The only one different point is that the head part 35f of the screw 30f is straight rod 355 having a ball head 354 located at the top end of the head part. The ball head 354 has a diameter larger than which of the rod 355 of the head part 35f so as to substantially make the rod 355 to be the neck part of the screw 30f.

Figure 10:
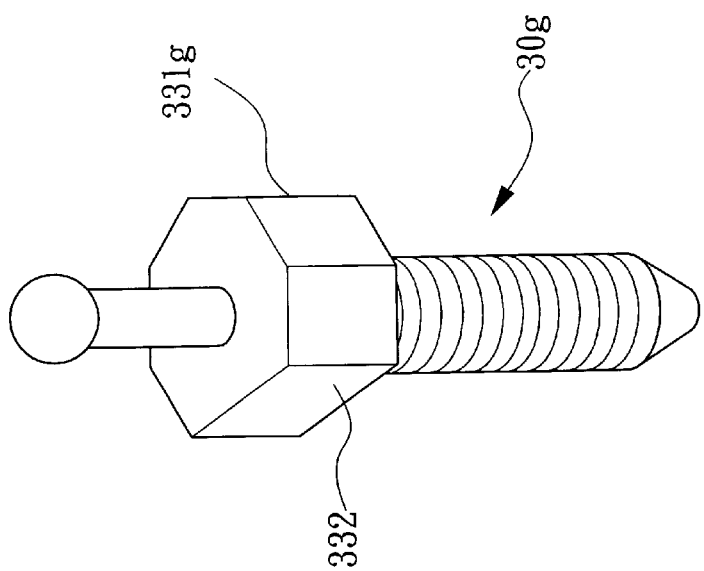
FIG. 10 is the tenth preferred embodiment for the screw device according to the invention for orthodontic treatment.

FIG. 10 is the tenth preferred embodiment for the screw device according to the invention for orthodontic treatment. In this preferred embodiment, most elements of the screw 30g are same as those of the embodiment shown in FIG. 9C, so a repetitious description is skipped herein. The only one different point is that the contour of the platform part 33g of the screw 30g is a polygon contour 331g having a binding area 332 formed at a side portion of the polygon contour 331g of the platform part 33g. The binding area 332 has an area relatively bigger than other side parts of the polygon contour 331g and can be attached with an additional component (not shown in this figure) choosing by the operator (doctor) for assisting orthodontic treatment.

FIG. 11 is the eleventh preferred embodiment for the screw device according to the invention for orthodontic treatment. In this preferred embodiment, most elements of the screw 30h are same as those of the embodiment shown in FIG. 10, so a repetitious description is skipped herein. The only one different point is that the binding area 332h of the platform part 33h of the screw 30h is attached with an orthodontic bracket 334 which is similar to the prior-art orthodontic bracket 14 shown in FIG. 1.

FIG. 12 is the twelfth preferred embodiment for the screw device according to the invention for orthodontic treatment. In this preferred embodiment, most elements of the screw 30i are same as those of the embodiment shown in FIG. 11, so a repetitious description is skipped herein. The only one different point is that the binding area 332i of the screw 30i is attached with a component 335 which has an elongated slot 3351 formed adjacent to the binding area 332i. Therefore, the elongated slot 3351 substantially forms a through hole for allowing the orthodontic archwire to pass through. In addition, the head part 35i of the screw 30i shown in FIG. 12 is a reversed L-shaped structure which is similar to the one shown in FIGS. 9A and 9B.

FIG. 13 is the thirteenth preferred embodiment for the screw device according to the invention for orthodontic treatment. In this preferred embodiment, most elements of the screw 30j are same as those of the embodiment shown in FIG. 11, so a repetitious description is skipped herein. The only one different point is that the binding area 332j of the screw 30j is attached with a component 336 which has an elongated slot 3361 formed on a surface away from to the binding area 332j. The cut section view of the slot 3361 is a circle having a diameter similar of slightly larger than which of the orthodontic archwire (not shown in this figure). Therefore, the elongated slot 3361 can allow the orthodontic archwire to pass therethrough. However, it is noted that the cut section view of the slot 3361 can also be a rectangular shape as which shown in FIG. 12.

Summarizing above description, the screw device according to the invention for orthodontic treatment indeed has following advantages:

(1) It is easy to operate. The head part and the neck part of the screw device according to the invention may be provided for hooking and hanging the spring directly without any worry of loosening off, and additional ligature wire is further unneeded for tying the spring.

(2) The spring won't make any irritation to the gingiva. The platform part of the screw device according to the invention has an advantage to prop the spring up the gingiva with an appropriate height to avoid any irritation.

(3) It is uneasy for the screw to loosen. The screw-body part of the screw of the invention may be completely screwed into the maxilla (or mandible) for keeping from loosening.

(4) The gingiva will be more beautiful after being healed over. The relatively larger area of the side surface of the outer contour of the platform part may provide a smooth surface for guiding the gingiva tissue to grow for making the surface of the gum be more beautiful after being healed over.

(5) It also has the function of orthodontic bracket. Slot is further formed at the head part of the screw of the invention for accommodating the orthodontic archwire to make the screw device of the invention further have the function similar to a orthodontic bracket capable of supporting the orthodontic archwire, aside from the function for hooking and hanging the spring.

Although the present invention has been described with reference to a preferred embodiment, it should be appreciated that various modifications and adaptations can be made without departing from the scope of the invention as defined in the claims.

What is claimed is:

1. A screw device for orthodontic treatment to be used with a spring comprising:
    a) a screw-body part having a diameter with external threads extending along a length;
    b) a platform part axially aligned with the screw-body part, the platform part having:
        i) a flat bottom plane adjacent to one end of the screw-body part and perpendicular to the screw-body part;
        ii) a flat top plane perpendicular to the screw-body part;
        iii) a plurality of side faces extending between the flat top and bottom planes and forming a polygon shaped outer periphery, the outer periphery bounding a platform part width in a lateral direction; and
        iv) a binding area formed on one of the plurality of side faces for adjoining an orthodontic component; and
    c) a head part having a neck with a uniform width, axially aligned with the screw-body part and extending outwardly from the top plane of the platform part at a first end thereof, the neck being configured to removably hook one end of the spring, thickness of the platform part determining the distance between the spring and the bottom plane of the platform part;
wherein the platform part width is larger than the width of the neck, and larger than the diameter of the screw-body part.

2. The screw device for orthodontic treatment according to claim 1, wherein the head part has an L-shape with a bend of 90 degrees relative to an axis of the screw device.

3. The screw device for orthodontic treatment according to claim 1, wherein the head part has a hook shape for securing the spring on the neck.

4. The screw device for orthodontic treatment according to claim 3, wherein the hook shape is formed by bending the head part in an arch shape of at least 360 degrees.

5. The screw device for orthodontic treatment according to claim 1, wherein the head part has a ball head connected to the neck at an end opposite the first end, the ball head having a diameter larger than the width of the neck.

6. The screw device for orthodontic treatment according to claim 1, further comprising an orthodontic bracket mounted on the binding area.

7. The screw device for orthodontic treatment according to claim 1, further comprising an orthodontic component mounted on the binding area, the orthodontic component having an elongated slot formed on a surface adjacent to the binding area, such that a through hole for an orthodontic archwire is formed between the orthodontic component and the binding area.

8. The screw device for orthodontic treatment according to claim 1, further comprising an orthodontic component mounted on the binding area, the orthodontic component having an elongated slot formed on a surface opposite the binding area.

9. The screw device for orthodontic treatment according to claim 8, wherein the elongated slot has a semi-circular cross section sized to accept an orthodontic archwire.

10. A screw device assembly for orthodontic treatment comprising:
    a) an orthodontic archwire;
    b) at least one orthodontic bracket adjoined to a tooth and having a slot sized to accept the orthodontic wire;
    c) at least one spring connected to one end of the orthodontic archwire at a first end thereof, the spring providing a pulling force on the orthodontic archwire; and
    d) a screw device spaced from the at least one orthodontic bracket, the screw device including:
        1) a screw-body part having a diameter with external threads extending along a length;
        2) a platform part axially aligned with the screw-body part, the platform part having:
            i) a flat bottom plane adjacent to one end of the screw-body part and perpendicular to the screw-body part;
            ii) a flat top plane perpendicular to the screw-body part;
            iii) a plurality of side faces extending between the flat top and bottom planes and forming a polygon shaped outer periphery, the outer periphery bounding a platform part width in a lateral direction; and
            iv) a binding area formed on one of the plurality of side faces for adjoining an orthodontic component; and
        3) a head part having a neck with a uniform width and axially aligned with the screw-body part and extending outwardly from the top plane of the platform part at a first end thereof, such that one end of the spring is removably hooked on the neck and a thickness of the platform part determines the distance between the spring and the bottom plane of the platform part;
wherein the platform part width is larger than the width of the neck, and larger than the diameter of the screw-body part.

11. The screw device assembly for orthodontic treatment according to claim 10, wherein the head part has an L-shape with a bend of 90 degrees relative to an axis of the screw device.

12. The screw device assembly for orthodontic treatment according to claim 10, wherein the head part has a hook shape securing the spring on the neck.

13. The screw device assembly for orthodontic treatment according to claim 12, wherein the hook shape is formed by bending the head part in an arch shape of at least 360 degrees.

14. The screw device assembly for orthodontic treatment according to claim 10, wherein the head part has a ball head connected to the neck at an end opposite the first end, the ball head having a diameter larger than the width of the neck.

15. The screw device assembly for orthodontic treatment according to claim 10, further comprising an orthodontic bracket mounted on the binding area.

16. The screw device assembly for orthodontic treatment according to claim 10, further comprising an orthodontic component mounted on the binding area, the orthodontic component having an elongated slot formed on a surface adjacent to the binding area, such that a through hole for an orthodontic archwire is formed between the orthodontic component and the binding area.

17. The screw device assembly for orthodontic treatment according to claim 10, further comprising an orthodontic component mounted on the binding area, the orthodontic component having an elongated slot formed on a surface opposite the binding area.

18. The screw device assembly for orthodontic treatment according to claim 17, wherein the elongated slot has a semi-circular cross section sized to accept an orthodontic archwire.

* * * * *